| United States Patent [19] | [11] | 4,089,884 |
|---|---|---|
| Shinohara et al. | [45] | May 16, 1978 |

[54] TRIS(TRIORGANOSILYLALKYL) PHOSPHITES AND METHOD FOR PREPARING THEM

[75] Inventors: Toshio Shinohara; Masatoshi Arai, both of Annaka; Kenichi Kojima, Shizuoka, all of Japan

[73] Assignees: Shin-Etsu Chemical Co.; Kumiai Chemical Industry Co., Ltd., both of Tokyo, Japan

[21] Appl. No.: 814,939

[22] Filed: Jul. 12, 1977

[30] Foreign Application Priority Data

Jul. 15, 1976 Japan .................................. 51-83454

[51] Int. Cl.$^2$ .............................................. C07F 7/10
[52] U.S. Cl. ...................... 260/448.2 N; 260/448.2 E; 424/184
[58] Field of Search ................. 260/448.2 N

[56] References Cited

U.S. PATENT DOCUMENTS

| 2,964,550 | 12/1960 | Seyferth | 260/448.2 N |
|---|---|---|---|
| 3,122,581 | 2/1964 | Pike | 260/448.2 N |
| 3,694,479 | 9/1972 | Groonhof | 260/448.2 N |

*Primary Examiner*—Paul F. Shaver
*Attorney, Agent, or Firm*—Toren, McGeady and Stanger

[57] ABSTRACT

A novel class of compounds, tris(triorganosilylalkyl) phosphites, represented by the general formula $[R_3Si(CH_2)_nO]_3P$ where R is a monovalent hydrocarbon group and $n$ is 1, 2 or 3. These novel compounds may be synthesized by dehydrochlorination reaction between a triorganosilyl-substituted alkanol and phosphorus trichloride in the presence of a tertiary amine. They have useful values as agricultural chemicals because of their biological activities and also as intermediate compounds in the preparation of certain medicines and chemicals.

9 Claims, No Drawings

TRIS(TRIORGANOSILYLALKYL) PHOSPHITES AND METHOD FOR PREPARING THEM

FIELD OF THE INVENTION

The present invention relates to a novel class of tris(triorganosilylalkyl) phosphites containing a number of silicon atoms and a phosphorus atom in the molecule. The invention relates also to a method of preparing the novel compounds.

SUMMARY OF THE INVENTION

The novel class of compounds provided herein are tris(triorganosilylalkyl) phosphites that have not been known and disclosed in any literature. The novel compounds are represented by the general formula $$[R_3Si(CH_2)_nO]_3P$$

Where R is a substituted or unsubstituted monovalent hydrocarbon group and n is a positive integer.

According to the present invention, the novel tris(triorganosilylalkyl) phosphites may be prepared by dehydrochlorination reaction between a triorganosilylalkanol and phosphorus trichloride in the presence of a dehydrochlorinating agent, such as a tertiary amine.

The novel compounds have biological activities suitable for agricultural chemicals. They are also useful as intermediate compounds in the synthetic preparation of certain organic compounds including medicines.

DETAILED DESCRIPTION OF THE PREFERRED EMBODIMENTS

In the general formula $[R_3Si(CH_2)_nO]_3P$ representing the novel tris(triorganosilylalkyl) phosphites of the present invention, the groups represented by symbol R being substituted or unsubstituted monovalent hydrocarbon groups, each being the same or different, are exemplified by alkyl groups, such as methyl, ethyl, propyl and butyl groups; alkenyl groups, such as vinyl and allyl groups; aryl groups, such as phenyl group; and those substituted monovalent groups by halogen atoms or other substituents in place of part or all of the hydrogen atoms in the above-named hydrocarbon groups and n is a positive integer or, in particular, 1, 2 or 3.

The examples belonging to the novel class of tris(triorganosilylalkyl) phospites within the above definition include the following compounds.

$[(CH_3)_3SiCH_2O]_3P$      (1)

$[(CH_3)_3Si(CH_2)_3O]_3P$      (2)

$[C_4H_9(CH_3)_2SiCH_2O]_3P$      (3)

$[CH_2=CH(CH_3)_2SiCH_2O]_3P$      (4)

$[C_6H_5(CH_3)_2SiCH_2O]_3P$      (5)

$[ClCH_2(CH_3)_2SiCH_2O]_3P$      (6)

The novel tris(triorganosilylalkyl) phosphites of the present invention may be prepared by several methods. For example, the compounds are synthesized by dehydrochlorination reaction between a triorganosilylalkanol corresponding to the desired phosphite and phosphorus trichloride in the presence of a tertiary amine as a dehydrochlorinating agent, such as trialkyl amines represented by the general formula $R'_3N$ where R' is an alkyl group.

As a further example, the novel compounds are produced by reacting an alkali metal, e.g. sodium or potassium salt of the triorganosilylalkanol with phosphorus trichloride in a suitable solvent with the formation of alkali chloride, e.g. NaCl or KCl.

Of the above two methods preferred is the former with respect of easiness in the synthetical operation as well as yield of product.

The reaction taking place in the former method is expressed by the following equation:

$$R_3Si(CH_2)_nOH + PCl_3 + 3R'_3N$$
$$\rightarrow [R_3Si(CH_2)_nO]_3P + 3R'_3N\cdot HCl$$

where R, R' and n are as defined herein above.

This reaction can be carried out by dropping a solution of phosphorus trichloride in an inert solvent into a mixture of the triorganosilylalkanol and the tertiary amine, optionally diluted with an inert solvent, under cooling, and, if necessary, and advantageously, by heating under reflux after the dropping is over. Subsequently amine hydrochloride which has been produced as a by-product is removed from the reaction mixture, and the resulting liquid portion is subjected to distillation, to finally obtain the desired tris(triorganosilylalkyl) phosphite.

The triorganosilylalkanols as the starting material in the above reaction are readily obtained by conventional methods. An example for the syntheses of the alkanol compound $(CH_3)_3SiCH_2OH$ is the following.

(a)    $(CH_3)_3SiCl + Cl_2 \rightarrow (ClCH_2)(CH_3)_2SiCl + HCl$
       (I)                  (II)

(b)    (II) $+ CH_3MgI \rightarrow ClCH_2Si(CH_3)_3 + ClMgI$
                           (III)

(c)    (III) $+ CH_3COOK \rightarrow (CH_3)_3SiCH_2\cdot OCOCH_3 + KCl$
                                           (IV)

(d)    (IV) $\xrightarrow{\text{hydrolysis}}$ $(CH_3)_3SiCH_2OH + CH_3COOH$

Another example for the synthesis of the alkanol compound $(CH_3)_3Si(CH_2)_3OH$ is the following.

(a)    $CH_3Si[(CH_2)_3Cl]Cl_2 + 2CH_3MgI \rightarrow$
       (V)

$(CH_3)_3Si(CH_2)_3Cl + 2ClMgI$
       (VI)

(b)    (VI) $+ CH_3COOK \rightarrow$ $(CH_3)_3Si(CH_2)_3\cdot OCOCH_3 + KCl$
       (VII)

(c)    (VII) $\xrightarrow{\text{hydrolysis}}$ $(CH_3)_3Si(CH_2)_3OH + CH_3COOK$ Illustrative of the tertiary amines used as the dehydrochlorinating agent in the reaction for the preparation of the tris(triorganosilylalkyl) phosphite of the present invention are triethylamine, pyridine, α-picoline, and tri(n-butyl)amine. Illustrative of suitable inert solvents are aromatic hydrocarbon solvents, such as benzene and toluene; aliphatic hydrocarbon solvents, such as hexane and octane; and ethers, such as diethyl ether and dibutyl ether.

The amounts of the triorganosilylalkanol and the tertiary amine used are each desired to be more than 3 moles per mole of phosphorus trichloride to be brought into reaction with them.

The temperature at which the reaction is carried out should be in the range from $-20$ to $+150°$ C or, preferably, from 0 to $+50°$ C.

The novel tris(triorganosilylalkyl) phosphites of the present invention are in general odorless in contrast to ordinary alkyl phosphites which have characteristic, unpleasant odor. They being biologically active compounds have an insecticidal activity against the noxious insects in rice crops, such as rice stem borers (larvae of Chilo Suppressalis Walker) and green rice leafhoppers (Nephotettix cincticeps Uhler). They are also useful as intermediate compounds in the synthetical preparation of various kinds of medicines and agricultural chemicals. Furthermore, they are effective as flame retardants when incorporated in plastic materials.

Further details of the synthesis of the novel compounds in accordance with the present invention and the identification of them will be apparent from the following examples.

EXAMPLE 1

Into a glass flask of 1 liter capacity provided with a stirrer, a thermometer and a reflux condenser were introduced 192 g (1.84 moles) of trimethylsilylmethyl alcohol, 202 g (2.00 moles) of triethylamine and 300 ml of benzene. The flask was submerged in an ice water bath. A solution of 80 g (0.58 moles) of phosphorus trichloride in 200 ml of benzene was dropped into the mixture in the flask over a period of about 2 hours. During the reaction the temperature of the reaction mixture was maintained between 0° and 10° C. The thus treated reaction mixture was then heated under reflux for 3 hours, to complete the intended reaction. Thereupon the reaction mixture was filtrated to remove triethylamine hydrochloride as a by-product, and the resulting filtrate was subjected to distillation to obtain 163.2 g of a product with fractional boiling at 89° to 91° C under the reduced pressure of 1.5 mmHg.

The product obtained above was subjected to elementary analysis, NMR spectral analysis, and measurement of density and refractive index. The results were as follows.

Elementary analysis:

|  | As measured | As calculated, as $[(CH_3)_3SiCH_2O]_3P$ |
|---|---|---|
| Si | 24.80% | 24.74% |
| C | 42.35% | 42.31% |
| H | 9.73% | 9.77% |
| O | 14.12% | 14.09% |
| P | 9.13% | 9.09% |
| NMR spectrum: | $(CH_3)_3-$ | 0.10 (δ) singlet |
|  | $\equiv SiCH_2OP\equiv$ | 3.23 (δ) doublet |
| Density, $d_4^{20}$: | 0.8856 | |
| Refractive index | $n_D^{25}$: | 1.4365 |

It was concluded from the above data that the product was a compound expressed by the structural formula $[(CH_3)_3SiCH_2O]_3P$. The yield of product was 82.6% of the theoretical.

EXAMPLE 2

The same flask as used in Example 1 was charged with 132 g (1.00 mole) of trimethylsilylpropyl alcohol, 152 g (1.50 moles) of triethylamine and 300 ml of benzene, and the flask was submerged in an ice water bath. Then a solution of 41.2 g (0.3 moles) of phosphorus trichloride in 200 ml of benzene was dropped into the mixture in the flask over a period of about 2 hours, throughout which the temperature of the reaction mixture remained between 0° and 10° C. The thus treated reaction mixture was then heated under reflux for 3 hours, to complete the intended reaction. Thereupon the reaction mixture was filtrated to remove triethylamine hydrochloride as a by-product, and the resulting filtrate was subjected to distillation to obtain 93.2 g of a product with fractional boiling at 158° to 159° C under the reduced pressure of 1.0 mmHg.

The product thus obtained was subjected to elementary analysis, NMR spectral analysis, and measurement of density and refractive index, with the results shown below.

Elementary analysis:

|  | As measured | As calculated, as $[(CH_3)_3Si(CH_2)_3O]_3P$ |
|---|---|---|
| Si | 19.80% | 19.84% |
| C | 50.92% | 50.90% |
| H | 10.70% | 10.68% |
| O | 11.28% | 11.29% |
| P | 7.30% | 7.29% |
| NMR spectrum: | $(CH_3)_3Si-$ | 0.04 (δ) singlet |
|  | $\equiv SiCH_2OP\equiv$ | 3.58 (δ) quartet |
| Density, $d_4^{20}$: | 0.8764 | |
| Refractive index; | $n_D^{25}$: | 1.4481 |

It was concluded from the above data that the product was a compound expressed by the structural formula $[(CH_3)_3Si(CH_2)_3O]_3P$. The yield was 73.2% of the theoretical.

EXAMPLE 3

The same flask as used in Example 1 was charged with 146 g (1.00 mole) of n-butyldimethylsilylmethyl alcohol, 152 g (1.50 moles) of triethylamine and 300 ml of benzene, and the flask was submerged in an ice water bath. Then a solution of 41.2 g (0.3 moles) of phosphorus trichloride in 200 ml of benzene was dropped into the mixture in the flask over a period of about 2 hours, throughout which the temperature of the reaction mixture was maintained between 0° and 10° C. The thus treated reaction mixture was then heated under reflux for 3 hours, to complete the intended reaction. Thereupon the mixture was filtrated to remove triethylamine hydrochloride as a by-product, and the resulting filtrate was subjected to distillation to obtain 113.8 g of a product with fractional boiling at 163° to 166° C under the reduced pressure of 1.0 mmHg.

The product thus obtained was subjected to elementary analysis, NMR spectral analysis and measurement of density and refractive index with the following results.

Elementary analysis:

|  | As measured | As calculated, as $[C_4H_9(CH_3)_2SiCH_2O]_3P$ |
|---|---|---|
| Si | 18.06% | 18.05% |

|   | As measured | As calculated, as $[C_4H_9(CH_3)_2SiCH_2O]_3P$ |
|---|---|---|
| C | 54.03% | 54.03% |
| H | 11.05% | 11.01% |
| O | 10.30% | 10.28% |
| P | 6.66% | 6.63% |
| NMR spectrum: | $-(CH_3)_2Si-$ | 0.10 (δ) singlet |
|  | $=SiCH_2OP=$ | 3.23 (δ) singlet |
| Density, $d_4^{20}$: | 0.8834 |  |
| Refractive index, $n_D^{25}$: |  | 1.4521 |

It was concluded from the above data that the product was a compound expressed by the structural formula $[C_4H_9(CH_3)_2SiCH_2O]_3P$. The yield was 81.3% of the theoretical.

What is claimed is:

1. A tris(triorganosilylalkyl) phosphite represented by the general formula $[R_3Si(CH_2)_nO]_3P$ where R is a substituted or unsubstituted monovalent hydrocarbon group and $n$ is a positive integer.

2. The tris(triorganosilylalkyl) phosphite as claimed in claim 1 wherein the group represented by symbol R is an alkyl group.

3. The tris(triorganosilylalkyl) phosphite as claimed in claim 1 wherein the positive integer expressed by symbol $n$ is 1, 2 or 3.

4. Tris(trimethylsilylmethyl) phosphite expressed by the formula $[(CH_3)_3SiCH_2O]_3P$.

5. Tris(trimethylsilylpropyl) phosphite expressed by the formula $[(CH_3)_3Si(CH_2)_3O]_3P$.

6. Tris(n-butyldimethylsilylmethyl) phosphite expressed by the formula $[(n-C_4H_9)(CH_3)_2SiCH_2O]_3P$.

7. A method for the preparation of a tris(triorganosilylalkyl) phosphite represented by the general formula $[R_3Si(CH_2)_nO]_3P$ where R is a substituted or unsubstituted monovalent hydrocarbon group and $n$ is a positive integer, which comprises subjecting a triorganosilylalkanol represented by the general formula $R_3Si(CH_2)_nOH$ where R and $n$ are as defined above, and phosphorus trichloride to dehydrochlorination reaction in the presence of a tertiary amine.

8. The method as claimed in claim 7 wherein the tertiary amine is a trialkylamine.

9. The method as claimed in claim 8 wherein the trialkylamine is triethylamine.

* * * * *